United States Patent [19]

Takahashi et al.

[11] Patent Number: 5,565,341
[45] Date of Patent: Oct. 15, 1996

[54] PROCESS FOR PRODUCING TREHALOSE

[75] Inventors: Eisaku Takahashi; Toshihiko Wada, both of Tokyo; Yutaka Konai, Machida, all of Japan

[73] Assignee: Kureha Chemical Industry Co., Ltd., Tokyo, Japan

[21] Appl. No.: 285,001

[22] Filed: Aug. 2, 1994

[30] Foreign Application Priority Data

Aug. 13, 1993 [JP] Japan ................................. 5-220472

[51] Int. Cl.$^6$ ............................. C12P 19/12; C12N 9/10
[52] U.S. Cl. ........................... 435/100; 435/97; 435/193; 435/194; 435/195; 435/200; 435/201; 536/123.13
[58] Field of Search ........................... 435/97, 100, 193, 435/194, 195, 200, 201; 536/123.13

[56] References Cited

U.S. PATENT DOCUMENTS

| | | | |
|---|---|---|---|
| 4,847,083 | 7/1989 | Clark | 424/642 |
| 5,077,205 | 12/1991 | Taniguchi et al. | 435/96 |
| 5,316,907 | 5/1994 | Lurie et al. | 435/195 |

FOREIGN PATENT DOCUMENTS

| | | |
|---|---|---|
| 0305981 | 3/1989 | European Pat. Off. |
| 2671099 | 7/1992 | France |
| 58-216695 | 12/1983 | Japan |
| 63-500562 | 3/1988 | Japan |
| 63-240758 | 10/1988 | Japan |
| 63-60998 | 11/1988 | Japan |

WO87/00196  1/1987  WIPO.

OTHER PUBLICATIONS

Kitamoto, Y., et al., "α–Glucose–1–phosphate formation by a novel trehalose phosphorylase from *Flammulina velutipes*," *FEMS Microbiology Letters*, 55 (1988) 147–150.

Murao et al., "Enzymatic Synthesis of Trehalose from Maltose," *Agric. Biol. Chem.*, 49 (7), 2113–2118, 1985.

Takuro Koga et al., "Purification and Some Properties of Sucrose Phosphorylase From *Leuconostoc mesenteroides*", *Agric. Biol. Chem.*, vol. 55(7), pp. 1805–1810, 1991.

Atsumi Kamogawa et al., "Purification and Properites of Maltose Phosphorylase From *Lactobacillus brevis*", *Agr. Biol. Chem.*, vol. 37 (12), pp. 2813–2819, 1973.

I. Schick et al., "Coenzyme–Independent Enzymatic Synthesis of α,α–Trehalose", *Biochem. Eng.* —*Stuttgart., Proc. Int. Symp. J.*, pp. 126–129, 2nd 1990 (Pub. 1991).

Primary Examiner—Herbert J. Lilling
Attorney, Agent, or Firm—Oliff & Berridge

[57] ABSTRACT

A process for producing trehalose from inexpensive saccharide raw materials via an enzymic method uses stable enzymes with high productivity. The process includes incubating a saccharide raw material and an inorganic phosphoric acid and/or a salt thereof in the presence of phosphorylase to produce α-glucose 1-phosphate, and contacting the produced α-glucose 1-phosphate with glucose in the presence of a trehalose phosphorylase to produce trehalose. The isolation and purification of trehalose is easier in comparison to conventional fermentation methods.

21 Claims, 1 Drawing Sheet

PROCESS FOR PRODUCING TREHALOSE

FIELD OF THE INVENTION

The present invention relates to a process for producing trehalose. More specifically, the present invention relates to a process for producing trehalose by use of inexpensive saccharide raw materials and stable enzymes with high productivity via an enzymic method wherein the isolation and purification of the end product are easier in comparison with fermentation methods,

BACKGROUND OF THE INVENTION

Recently, attention has been given to various oligosaccharides add efforts are being made to develop their use. Trehalose is a disaccharide widely distributed in animals, plants and microorganisms. It is proposed that trehalose be utilized as sweetening agents (Published Unexamined Japanese Patent Application No. 240758/1988), and agents for protecting proteins from drying (Published Unexamined Japanese Patent Application No. 50:0562/1988).

It is known that there are extraction methods, which make use of the natural sources of trehalose listed above. There are also microbiological fermentation methods, which make use of yeasts, Arthrobacter, Nocardia or the like. The known methods in the prior art, however, are minimally productive and not industrially feasible because they require complicated operations in the separation and purification of the desired saccharide products.

An enzymic method, in which trehalose is produced from maltose via β-glucose 1-phosphate, is disclosed in Japanese Patent Publication No. 60998/1988. This method, however, has disadvantages in view of the cost of maltose as well as the cost and availability of maltose phosphorylase. In addition, trehalose phosphorylase, which catalyzes the formation of trehalose from β-glucose 1-phosphate and glucose, lacks stability. Further, Euglena (green algae), the source of the trehalose phosphorylase, is not easy to culture.

Another enzymic method, in which trehalose is produced from α-glucose 1-phosphate and glucose around pH 7 in the presence of a trehalose phosphorylase obtained from *Flammulina velutipes,* is disclosed in FEMS Microbiology Letters, 55, 147–150 (1988). The trehalose phosphorylase from *Flammulina velutipes,* however, lacks stability, making its preparation rather difficult. The enzyme cannot sustain its activity at the temperature range necessary for industrial operations for an extended period of time. It therefore is concluded that the trehalose phosphorylase from *Flammulina velutipes* is not applicable to industrial use.

In short, although fermentation and enzymic methods are known in the prior art for producing trehalose besides extraction methods, the fermentation methods suffer from low productivity and complex isolation and purification of the end products, whereas the enzymic methods suffer from the high price of the substrate as well as the high price and poor stability of the enzyme. Thus, no industrial production of trehalose has heretofore been accomplished. It is desired to develop a process for producing trehalose by use of inexpensive substrates and enzymes of high productivity, ready availability and high stability, via an enzymic method wherein it is easier to isolate and purify the end product than in the fermentation methods.

SUMMARY OF THE INVENTION

An object of the present invention is to provide a process for producing trehalose by use of inexpensive saccharide raw materials and stable enzymes with high productivity via an enzymic method wherein the isolation and purification of the end products are easier than in fermentation methods.

The present inventors have discovered novel trehalose phosphorylases, which are unexpectedly stable and capable of producing trehalose from a α-glucose 1-phosphate and glucose, and subsequently succeeded in turning the discovery into the process herein disclosed.

The present invention provides a process for producing trehalose, which process comprises first reacting a saccharide raw material and an inorganic phosphoric acid and/or a salt thereof in the presence of a saccharide phosphorylase (hereinafter referred to as an α-phosphorylase) that is capable of catalyzing the formation of α-glucose 1-phosphate from the saccharide raw material and inorganic phosphoric acid and/or salt thereof, thus starting α-glucose 1-phosphate formation, and second, after allowing α-glucose 1-phosphate to accumulate to an appropriate amount, reacting glucose and α-glucose 1-phosphate in the presence of a trehalose phosphorylase that is capable of catalyzing the formation of trehalose from α-glucose 1-phosphate and glucose, thus producing trehalose by adding the trehalose phosphorylase and glucose to the reaction mixture without isolating α-glucose 1-phosphate.

In another aspect, the present invention provides a process for producing trehalose, which process comprises mixing (1) α-phosphorylase that is capable of catalyzing the formation of α-glucose 1-phosphate from a saccharide raw material and an inorganic phosphoric acid and/or a salt thereof, (2) a saccharide raw material, (3) an inorganic phosphoric acid and/or salt thereof, (4) glucose, and (5) trehalose phosphorylase that is capable of catalyzing the formation of trehalose from α-glucose 1-phosphate and glucose in any order and reacting the mixture to produce trehalose.

In another aspect, the present invention provides a process for producing trehalose, which process comprises reacting a saccharide raw material and an inorganic phosphoric acid and/or a salt thereof, the mol/weight ratio of the latter over the former preferably being in a specific range, and reacting α-glucose 1-phosphate thus obtained and glucose in the presence of trehalose phosphorylase to produce trehalose with high efficiency.

DETAILED DESCRIPTION OF THE INVENTION

Figure 1:
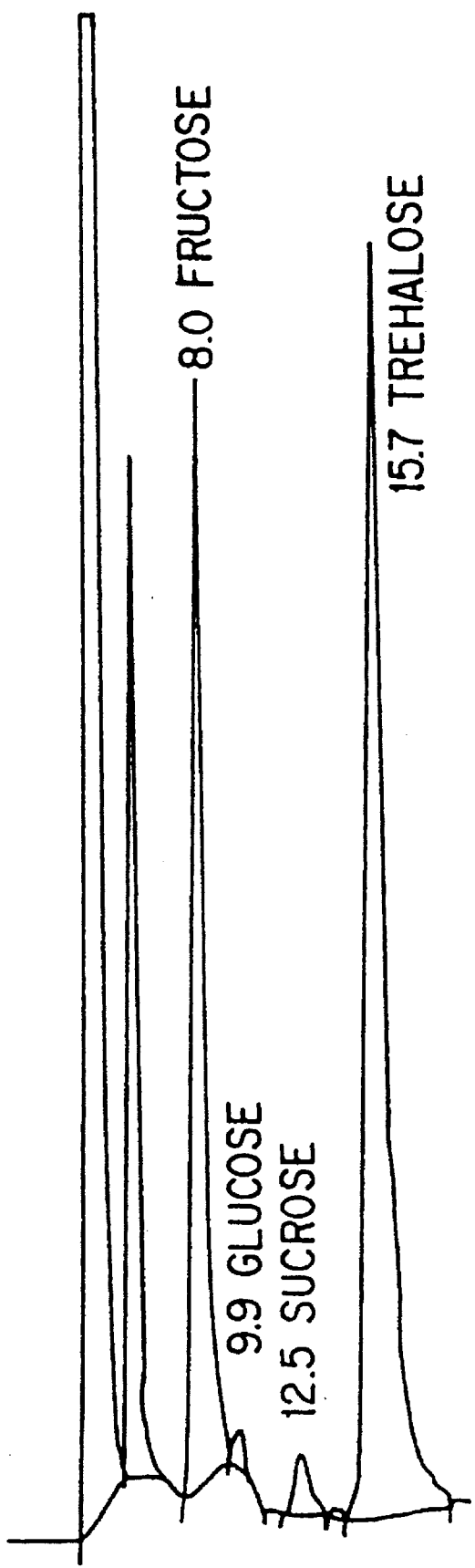
FIG. 1 illustrates a high performance liquid chromatographic profile of the enzymic reaction products obtained in Example 6.

The present invention relates to a process for producing trehalose, which process comprises incubating a saccharide raw material with an inorganic phosphoric acid and/or a salt thereof in the presence of an α-phosphorylase to produce α-glucose 1-phosphate, and incubating α-glucose 1-phosphate with glucose in the presence of a trehalose phosphorylase to produce trehalose.

The saccharide raw material for α-glucose 1-phosphate, is, for example, starch, glycogen, dextrin, 1,4-α-D-glucan, cellobiose, cellodextrin, 1,4-β-D-oligoglucan, laminaribiose, laminarin, 1,3-β-D-oligoglucan, 1,3-β-D-glucan, sucrose and the like.

The α-phosphorylase is, for example, starch phosphorylase, glycogen phosphorylase, 1,4-α-D-glucan phosphorylase, cellobiose phosphorylase, cellodextrin phosphorylase, 1,4-β-D-oligoglucan phosphorylase, laminaribiose phosphorylase, laminarin phosphorylase, 1,3-β-D-oligoglucan phosphorylase, 1,3-β-D-glucan phosphorylase, sucrose phosphorylase and the like according to the saccharide raw material used.

As for the trehalose phosphorylase, any enzyme may be used regardless of its origin as long as it is capable of producing trehalose from α-glucose 1-phosphate and glucose and, at the same time, possesses sufficient stability. The sources of the trehalose phosphorylase include, but are not limited to, fruit body, mycelium, or liquid mycelium culture of Basidiomycetes such as Schizophyllum, Pleurotus, Lyophyllum, Grifola, Agaricus, Trametes, Coriolus, Trichaptum and Lenzites. Preferably, the sources of the trehalose phosphorylase include fruit body, mycelium, or liquid mycelium culture of Basidiomycetes such as *Schizophyllum commune, Pleurotus ostreatus, Lyophyllum ulmarium, Grifola frondosa, Agaricus bisporus, Trametes versicolor, Coriolus versicolor, Trametes hirsuta, Coriolus hirsutus, Coriolus consors, Trichaptum biforme, Lenzites betulina* and the like.

The sources of the trehalose phosphorylase may be substantiated as fruit body, mycelium, or liquid mycelium culture of the strains of Basidiomycetes deposited with Japanese Patent Microorganism Depository Authority; National Institute of Bioscience and Human-Technology (NIBH), Agency of Industrial Science and Technology, Ministry of International Trade and Industry, Tsukuba-shi, Ibaraki, Japan. Deposited are:

*Schizophyllum commune* FERM P-1744, *Pleurotus ostreatus* FERM P-1746, *Lyophyllum ulmarium* FERM P-985, *Grifola frondosa* FERM BP-35, *Agaricus bisporus* FERM P-1748, *Coriolus versicolor* FERM P-2412, *Coriolus hirsutus* FERM P-2711, *Coriolus consors* FERM P-988, *Trichaptum biforme* FERM P-2712, *Lenzites betulina* FERM BP-27 and the like.

The sources of the trehalose phosphorylase are also substantiated as fruit body, mycelium, or liquid mycelium culture of the strains of Basidiomycetes such as *Trametes versicolor* ATCC 20547, *Trametes hirsuta* ATCC 20561, *Coriolus consors* ATCC 20565, *Coriolus pargamenus* ATCC 20562 and the like.

The strains listed above were identified and named in compliance with "Colored Illustrations of Mushrooms of Japan", by Rokuya Imazeki and Tsuguo Hongo (Vols. I, 1987, and II, 1989, Hoikusha, Osaka, Japan), "Coloured Illustrations of Fungi of Japan", by the same authors (1957, sequel 1965, Hoikusha, Osaka, Japan), and "Mycological Flora of Japan", by Seiya Ito (Vol. II Part 1, 1936, Part 2, 1939, Part 3, 1950, Part 4, 1955, and Part 5, 1959, Yokendo, Tokyo, Japan).

Parts of rotten plant bodies on which the fungi sit, fruit body tissues of the fungi, or their spores are inoculated to a suitable nutrient medium and incubated at a proper temperature for several weeks. The same treatment was repeated a few times to obtain purified strains which were then utilized in the experiments for the present invention and deposited with said Patent Microorganism Depository Authority: NIBH, Japan.

The sources of the trehalose phosphorylase of the present invention may also include mutants of the strains capable of producing the trehalose phosphorylase.

The trehalose phosphorylase of the present invention may also include trehalose phosphorylase or modified trehalose phosphorylase produced by a host which has been subjected to the transfer of a gene having the sequence coding for the trehalose phosphorylase or modified trehalose phosphorylase, incubated to express the ability of producing the trehalose phosphorylase or modified trehalose phosphorylase.

Strains of the Basidiomycetes listed above may be cultured by a conventional method to produce the trehalose phosphorylase. For example, a strain may be cultured in a medium of pH 5.5 to 7.0 containing 0.1 to 5 wt. % yeast extract, 0.1 to 5 wt. % malt extract and 0.5 to 10 wt. % glucose for several days with shaking, followed by collection of organisms by centrifugation to obtain enzyme sources. Further, fruit body obtained from Basidiomycetes cultures in conventional sawdust media and the like, or commercially available mushrooms such as "Hiratake", "Bunasimeji", "Maitake" (all Japanese trivial names), and French mushroom can be used as the enzyme source.

The trehalose phosphorylase of the present invention is prepared from its source as follows: Basidiomycetes mycelia or fruit bodies are disrupted in a buffer solution such as a phosphate buffer, separated off insolubles to give a crude enzyme solution. The crude enzyme solution can be used for the production of trehalose as it is. Further isolation and purification, however, are preferred. The crude enzyme solution may be purified by means of conventional methods or techniques for the purification of proteins, such as salting-out with ammonium sulfate, precipitation by the addition of organic solvent, ion exchange resin adsorption, membrane dialysis, membrane ultrafiltration, hydroxyapatite adsorption, and hydrophobic carriers. Further, although both purified and crude enzymes may be used as they are, they may be immobilized with known techniques such as carrier coupling, cross-linking, gel entrapping and microencapsulation. Living cells may be also entrapped in matrices of polyacrylamide, κ-carrageenan, alginic acid, photo-crosslinkable resin prepolymers and the like to provide biocatalysts.

In an aspect of an embodiment of the present invention, a saccharide raw, material is allowed to react with an inorganic phosphoric acid and/or a salt thereof in the presence of an α-phosphorylase for a given length of time to produce α-glucose 1-phosphate, which, without being isolated, is then allowed to react with glucose in the presence of a trehalose phosphorylase by introducing glucose and trehalose phosphorylase to the reaction system to produce trehalose and an inorganic phosphoric acid.

In another aspect of an embodiment of the present invention, a saccharide raw material, an inorganic phosphoric acid and/or a salt thereof, an α-phosphorylase, glucose, and a trehalose phosphorylase are mixed in aqueous solution in any order and allowed to react to produce trehalose and an inorganic phosphoric acid.

A third aspect of an embodiment of the present invention is exemplified by conducting the formation of α-glucose 1-phosphate from a saccharide raw material and that of trehalose from α-glucose 1-phosphate and glucose independently. However, the necessity of separating and purifying α-glucose 1-phosphate as well as of using the stoichiometric amount of inorganic phosphoric acid and/or salt thereof to the saccharide raw material could bring about some difficulty.

In the process of the present invention, enzymes do not interact each other. Further, enzymes are not susceptible to inhibition by the substrate and product of the reactions. The absence of the interaction between the two enzymes makes it possible for, once the formation of α-glucose 1-phosphate by the catalytic action of α-phosphorylase has started, glucose and the trehalose phosphorylase to be introduced to the reaction system at any time. In this manner, glucose reacts with the α-glucose 1-phosphate which has already been produced, as well as with the α-glucose 1-phosphate which is being produced currently, to give trehalose, the desired product, and inorganic phosphoric acids, which can be recycled to react with the saccharide raw material. The required amount of inorganic phosphoric acid and/or salt thereof is reduced to a level far lower than the stoichiometric level, making the process of the present invention advantageous from the practical viewpoint.

In the process of the present invention, there are no restrictions in terms of the timing of the addition of glucose because glucose is inert except for the reaction with α-glucose 1-phosphate. Glucose can be introduced to the reaction system along with the saccharide raw material, inorganic acids and/or salts thereof, and α-phosphorylase in the very beginning. Glucose can also be introduced to the reaction system along with the trehalose phosphorylase at any time after the formation of α-glucose 1-phosphate has started. Glucose can also be introduced to the reaction system by itself at any time.

Preferably, all the substrates and the enzymes are mixed at once to get the reaction started. The reason is that mixing all the ingredients at once corresponds to diminishing the time lag between the start of the formation of α-glucose 1-phosphate and that of trehalose to zero, thus maximizing α-glucose 1-phosphate's conversion to trehalose, and at the same time minimizing α-glucose 1-phosphate's loss in useless side reactions because α-glucose 1-phosphate is not left without glucose in any time.

There are no restrictions on the order of mixing the substrates and the enzymes. In an extreme case, even the trehalose phosphorylase can be the first to be introduced into the reactor.

In an embodiment of the process of the present invention, the saccharide raw material for α-glucose 1-phosphate may be used in a concentration range of 0.1 to 75 kg in 100 l of the whole of the reaction mixture. For example, starch may be used in a concentration range of 0.5 to 50 kg, preferably 1 to 30 kg; sucrose, 0.1 to 75 kg, preferably 1 to 50 kg in 100 l of the whole of the reaction mixture, respectively. The whole of the reaction mixture is defined as the volume of the reaction mixture at the point when all the ingredients have been placed at the temperature at which the reaction is conducted.

In the process of the present invention, glucose may be used in a weight/volume concentration range of 0.01 to 50 kg, preferably 1 to 25 kg in 100 l of the whole of the reaction mixture.

The inorganic phosphoric acid and/or salt thereof used in the process of the present invention may include orthophosphoric acid, sodium phosphate, potassium phosphate, sodium dihydrogen phosphate, and potassium dihydrogen phosphate. The acids and/or the salts are preferably used in the form of a phosphate buffer.

In the process of the present invention, the inorganic phosphoric acid and/or salt thereof may be used in a range of 0.1 mmol to 6 mol, preferably 1 mmol to 0.5 mol for 1 kg of the saccharide raw material.

In the process of the present invention, the α-phosphorylase may be used in 0.1 units or more, preferably 1 unit or more; and the trehalose phosphorylase 0.1 units or more, preferably 1 unit or more, respectively, for 1 kg of the saccharide raw material for α-glucose 1-phosphate. There exists no upper limit for the amount of the enzymes useable. The optimal amount of the enzymes is decided from an economical standpoint.

In the process of the present invention, the formation of α-glucose 1-phosphate may be conducted at pH 2 to 10, preferably 4 to 9, in a temperature range of 10° to 80° C., preferably 15° to 60° C. The formation of trehalose from α-glucose 1-phosphate may be conducted at pH 2 to 10, preferably 4 to 9, in a temperature range of 10° to 80° C., preferably 15° to 60° C.

In an embodiment of the process of the present invention, the reactions may be conducted under reduced, normal or high pressure. When conducted under reduced pressure, 0.5 to 1 kg/cm$^2$-G may be applied, whereas, when conducted under high pressure, 1 to 10 kg/cm$^2$-G may be applied.

After a desired amount of trehalose is accumulated in the reaction system according to the process of the present invention, the enzyme may be inactivated by conventional procedures, for example heating, if necessary. The reaction mixture may be subjected to centrifugal separation, filtration, or the like to remove insolubles. The resultant supernatant, being a saccharide mixture consisting of mainly trehalose, may be used as it is for some purposes, or may be purified to give trehalose if necessary. In an example of purification, the supernatant may be treated with charcoal to adsorb trehalose, eluted with a 20% aqueous ethanol solution, and treated with an anion type ion-exchange resin such as Dowex-1™ (The Dow Chemical Company, U.S.A.), CM-Cellulose (Wako Jun-yaku K. K., Japan) or the like to give a purified sugar solution. The sugar solution thus obtained may be further purified by adsorption on a boric acid type ion-exchange resin, followed by elution with an aqueous potassium borate solution or the like, and concentration to give trehalose crystals.

In accordance with the present invention, by the catalytic action of α-phosphorylase, commercially available inexpensive saccharides such as starch, sucrose or cellobiose can be easily and advantageously converted into α-glucose 1-phosphate, which in turn can be easily and advantageously reacted with glucose to give trehalose by the catalytic action of the novel trehalose phosphorylase. The trehalose phosphorylase used in the present invention excels not only in trehalose production but also in stability. Furthermore, the trehalose phosphorylase of the present invention can be easily prepared. Thus the trehalose phosphorylase of the present invention is suitable for an industrial production of trehalose.

EXAMPLES

The following examples are intended to illustrate the invention in further detail and should by no means be construed as limiting the scope of the invention.

PREPARATION EXAMPLE 1

(Preparation of trehalose phosphorylase)

To 295 g of fresh commercial 'Maitake' (Japanese trivial name for the fruit body of *Grifola frondosa*) is added 600 ml of 20 mM Tris-HCl buffer (pH 7.5, containing 20% glycerol, 1 mM EDTA, and 1 mM dithiothreitol), followed by disruption and extraction in a Waring Blender™ (Dynamics Corporation of America, U.S.A.). A centrifugal separation of insolubles from the mixture gives 780 ml of a crude enzyme solution as supernatant. Ammonium sulfate is added to the crude enzyme solution to 60% saturation and the resultant precipitate is collected by a centrifugal separation, dissolved in a 20 mM Tris-HCl buffer solution containing 30% ammonium sulfate, loaded on a column (15 mm ID×140 mm L) packed with 24 ml of Butyl-Toyopearl™ 650 (Tosoh K. K., Japan) equilibrated with the same buffer solution, washed with the same buffer solution, and eluted with a linear gradient solvent system of 30% to 0% ammonium sulfate in 20 mM Tris-HCl buffer (total volume, 250 ml), and collected into fractions. The fractions with the trehalose phosphorylase activity are combined, dialyzed against a 20 mM citric acid—NaOH buffer solution (pH 6.0, containing 20% glycerol, 1 mM EDTA, and 1 mM dithiothreitol), loaded on a column (15 mm ID×110 mm L) packed with 20 ml of AF-Blue Toyopearl™ 650 (Tosoh K. K., Japan) equilibrated with the citric acid—NaOH buffer solution, washed with the citric acid—NaOH buffer solution, eluted with a linear gradient solvent system of 0 to 0.5 M KCl in a 20 mM citric acid—NaOH buffer solution (total volume, 200 ml), and collected into fractions. The fractions with the trehalose phosphorylase activity are combined and concentrated by means of a hollow fiber ultrafiltration apparatus to give 3.1 ml of an enzyme solution, the total and specific activities of which are 10.8 unit/ml and 3.48 unit/mg-protein, respectively.

The enzymic activity is determined according to the following procedure: 10.8 g of trehalose, 860 mg of glutathione, and 17.2 mg of $Na_2EDTA$ are dissolved in a 57 mM potassium phosphate buffer solution (pH 7.0) to prepare 100 ml of a solution. A mixture of 1.40 ml of the thus prepared solution, 100 μl of a 20 mM $NADP^+$ solution, 100 μl of a 26 mM magnesium chloride solution, 100 μl of a 1.34 mM glucose 1,6-diphosphate solution, 100 μl of a 31 unit/ml phosphoglucomutase solution, 100 μl of a 35 unit/ml glucose 6-phosphate dehydrogenase solution, and 100 μl of a sample solution is incubated at 30° C. and the quantity of produced NADPH is monitored consecutively by means of absorption spectrophotometry at 340 nm. One unit refers to the amount of enzyme which is capable of producing 1 μmol of NADPH for 1 min. under the conditions.

PREPARATION EXAMPLE 2

(Preparation of trehalose phosphorylase)

In each of five 300 ml Erlenmyer flasks is placed 100 ml of a nutrient medium containing 0.75% yeast extract and 5.0% glucose, sterilized at 120° C. for 20 min., inoculated with a strain selected from a group tabulated in Table 1, and cultured with shaking at 26° C. for 3 days. The mycelium thus obtained is collected by centrifugation, mixed with ca. 200 ml of a 20 mM phosphate buffer solution (pH 7.0), disrupted and extracted in a Waring Blender™ (Dynamics Corporation of America, U.S.A.), separated off insolubles by centrifugation to give a crude enzyme solution. The crude enzyme solution is loaded on a column packed with DEAE-Toyopearl™ 650C (Tosoh K. K., Japan) equilibrated with a 20 mM phosphate buffer solution (pH 7.0), washed with the same buffer solution, and eluted with a linear gradient solvent system of 0 to 0.5 M KCl in a 20 mM phosphate buffer solution (total volume, 400 ml) to give an enzyme solution. Table 1 shows the volume, the activity, the total activity, and the specific activity of the enzyme solution prepared from each strain.

TABLE 1

| Strain | Volume ml | Activity Unit/ml | Total Activity Unit | Specific Activity Unit/mg-Protein |
|---|---|---|---|---|
| Coriolus versicolor FERM P-2412 | 73 | 0.084 | 6.1 | 0.14 |

TABLE 1-continued

| Strain | Volume ml | Activity Unit/ml | Total Activity Unit | Specific Activity Unit/mg-Protein |
|---|---|---|---|---|
| Coriolus hirsutus FERM P-2711 | 69 | 0.071 | 4.9 | 0.23 |
| Trichaptum biforme FERM P-2712 | 51 | 0.071 | 3.6 | 0.086 |
| Lenzites betulina FERM BP-27 | 35 | 0.11 | 3.9 | 0.35 |
| Schizophyllum commune FERM P-1744 | 80 | 0.033 | 2.6 | 0.15 |

PREPARATION EXAMPLE 3

(Preparation of trehalose phosphorylase)

To 100 g of each selected from a group consisting of fresh fruit bodies of mushroom (Agaricus bisporus), 'Maitake' (Japanese trivial name for Grifola frondosa), 'Hiratake' (Japanese trivial name for Pleurotus ostreatus), and 'Bunashimeji' (Japanese trivial name for Lyophyllum ulmarium) is added ca. 150 ml of a 20 mM phosphate buffer solution (pH 7.0, containing 20% glycerol, 1 mM EDTA, and 1 mM dithiothreitol), disrupted and extracted in a Waring Blender™ (Dynamics Corporation of America, U.S.A.), and separated off insolubles by centrifugation to give a crude enzyme solution as supernatant. The crude enzyme solution is loaded on a column packed with 20 ml of QAE-Toyopearl™ (Tasoh K. K., Japan), washed with the same buffer solution, eluted with a linear gradient solvent system of 0 to 0.5 M KCl in a 20 mM phosphate buffer solution (total volume, 200 ml), and collected into fractions. The fractions with the trehalose phosphorylase activity are combined and concentrated by means of a hollow fiber ultrafiltration apparatus to give an enzyme solution. Table 2 shows the volume, the activity, the total activity, and the specific activity of the enzyme solution prepared from each strain.

TABLE 2

| Strain | Volume ml | Activity Unit/ml | Total Activity Unit | Specific Activity Unit/mg-Protein |
|---|---|---|---|---|
| Agaricus bisporus Mushroom | 4.0 | 2.4 | 9.5 | 0.13 |
| Grifola frondosa Maitake | 10 | 4.75 | 48 | 0.37 |
| Pleurotus ostreatus Hiratake | 5.3 | 5.1 | 27 | 0.45 |
| Lyophyllum ulmarium Bunashimeji | 10 | 0.56 | 5.6 | 0.027 |

PREPARATION EXAMPLE 4

(Preparation of α-phosphorylase)

Potatoes (350 g) are minced and mixed with 200 ml of a 20 mM phosphate buffer solution (pH 7.0, containing 20% glycerol, 1 mM EDTA, and 1 mM dithiothreitol), disrupted and extracted in a Waring Blender™ (Dynamics Corporation of America, U.S.A.), filtered off starch through gauze, and separated off insolubles by centrifugation to give 400 ml of a crude enzyme solution as supernatant. The crude enzyme solution is loaded on a column packed with 100 ml of DEAE-Toyopearl™ (Tosoh K. K., Japan) equilibrated with a 20 mM phosphate buffer solution (pH 7.0), eluted with a linear gradient solvent system of 0 to 0.5 M KCl in a 20 mM phosphate buffer solution (total volume, 600 ml), and collected into fractions of 7.6 ml each. The fractions No. 31 through 41 show the α-phosphorylase activity. The fractions with the α-phosphorylase activity (84 ml) are combined and concentrated by means of a hollow fiber ultrafiltration apparatus to give 5.4 ml of an enzyme solution, the activity of which is 32.3 unit/ml.

The enzymic activity is determined according to the following procedure: 1.72 g of glutathione, and 34.2 mg of $Na_2EDTA$ are dissolved in a 114 mM potassium phosphate buffer solution (pH 7.0) to prepare 100 ml of a solution. A mixture of 700 μl of the solution, 700 μl of a thermally dissolved 5.72% starch solution, 100 μl of a 20 mM $NADP^+$ solution, 100 μl of a 26 mM magnesium chloride solution, 100 μl of a 1.34 mM glucose 1,6-diphosphate solution, 100 μl of a 31 unit/ml phosphoglucomutase solution, 100 μl of a 35 unit/ml glucose 6-phosphate dehydrogenase solution, and 100 μl of a sample enzyme solution is incubated at 30° C. and the quantity of produced NADPH is monitored consecutively by means of absorption spectrophotometry at 340 nm. One unit refers to the amount of enzyme which is capable of producing 1 μ mol of NADPH for 1 min. under the conditions.

EXAMPLE 1

A mixture of 750 μl of a 200 mM sucrose solution, 375 μl of a 400 mM potassium phosphate buffer solution (pH 6.0), 300 μl of a 500 mM 2-[N-morpholino]ethanesulfonic acid buffer (pH 6.0, hereinafter referred to as 'MES buffer'), 50 μl of a 17.8 unit/ml sucrose phosphorylase (Sigma, U.S.A.) solution, and 25 μl of purified water is incubated at 35° C. for 10 hours in a capped reactor. The resultant mixture is heated to inactivate the enzyme, subjected to the analytical procedure described below and found to contain 75 mM of α-glucose 1-phosphate. The yield of α-glucose 1-phosphate from sucrose is calculated to be 75 mol %.

The concentration of α-glucose 1-phosphate is determined according to the following procedure: 17.1 mg of $Na_2EDTA$ is dissolved in 47 mM potassium phosphate buffer (pH 7.0) to prepare 100 ml of a solution. A mixture of 2.5 ml of the solution, 100 μl of a 14.8 mM $NADP^+$ solution, 100 μl of a 26 mM magnesium chloride solution, 100 μl of a 1.34 mM glucose 1,6-diphosphate solution, 50 μl of a 31 unit/ml phosphoglucomutase solution, 50 μl of a 35 unit/ml glucose 6-phosphate dehydrogenase solution, and 100 μl of a sample solution is incubated at 30° C. for 30 min. and subjected to spectrophotometric measurement at 340 nm to give the amount of produced NADPH, thus determining indirectly the amount of α-glucose 1-phosphate in the sample solution.

EXAMPLE 2

A mixture of 1150 μl of the α-glucose 1-phosphate solution prepared in Example 1 (in which the enzyme is inactivated by heating), 300 μl of a 500 mM glucose solution, 40 μl of the 10.8 unit/ml trehalose phosphorylase solution prepared in Preparation Example 1, and 10 μl of purified water is incubated at 35° C. for 21 hours in an Eppendorf™ tube. The resultant mixture is heated to inactivate the enzyme, subjected to the analytical procedure described below and found to contain 33 mM of trehalose. The yield of trehalose from α-glucose 1-phosphate is calculated to be 57 mol %.

The concentration of trehalose is determined according to the following procedure: the reaction mixture is subjected to an HPLC analysis with a YMC-Pack™ Polyamine II column (4.6 mm ID×250 mm L, YMC K. K., Japan) kept at 35° C., 1 ml/min. of an acetonitrile—water (7:3) solvent, and a differential refractometer kept at 35° C. Trehalose shows a retention time of 15.7 minutes under the conditions.

EXAMPLE 3

The enzyme solution prepared from *Coriolus hirsutus* FERM P-2711 in Preparation Example 2 is concentrated by means of a hollow fiber ultrafiltration apparatus to give 2.0 ml of a 2.4 unit/ml trehalose phosphorylase solution. A mixture of 50 μl of the concentrated enzyme solution, 50 μl of a 500 mM sucrose solution, 50 μl of a 500 mM glucose solution, 10 μl of a 400 mM potassium phosphate buffer solution (pH 6.5), 50 μl of a 500 mM MES buffer solution (pH 6.5), 10 μl of a 11.5 unit/ml sucrose phosphorylase (Sigma, U.S.A.) solution, and 30 μl of purified water is incubated at 30° C. for 18 hours in an Eppendorf™ tube. The resultant mixture is heated to inactivate the enzymes, subjected to the analytical procedure described in Example 2 and found to contain 24 mM of trehalose. The yield of trehalose from sucrose is calculated to be 24 mol %.

EXAMPLE 4

A mixture of 24 μl of the 5.1 unit/ml trehalose phosphorylase solution prepared from *Pleurotus ostreatus* in Preparation Example 3, 50 μl of a 500 mM sucrose solution, 50 μl of a 500 mM glucose solution, 10 μl of a 400 mM potassium phosphate buffer solution (pH 6.5), 50 μl of a 500 mM MES buffer solution (pH 6.5), 10 μl of a 11.5 unit/ml sucrose phosphorylase (Sigma, U.S.A.) solution, and 56 μl of purified water is incubated at 30° C. for 36 hours in an Eppendorf™ tube. The resultant mixture is heated to inactivate the enzymes, subjected to the analytical procedure described in Example 2 and found to contain 29 mM of trehalose. The yield of trehalose from sucrose is calculated to be 29 mol %.

EXAMPLE 5

A mixture of 300 μl of a 500 mM sucrose solution, 300 μl of a 500 mM glucose solution, 150 μl of a 100 mM potassium phosphate buffer solution (pH 6.5), 300 μl of a 500 mM MES buffer solution (pH 6.5), 50 μl of the 10.8 unit/ml trehalose phosphorylase solution prepared in Preparation Example 1, 30 μl of a 17.8 unit/ml sucrose phosphorylase (Sigma, U.S.A.) solution, and 370 μl of purified water is incubated at 27.5° C. for 70 hours in an Eppendorf™ tube. The resultant mixture is heated to inactivate the enzymes, subjected to the analytical procedure described in Example 2 and found to contain 96 mM of trehalose. The yield of trehalose from sucrose is calculated to be 96 mol %.

EXAMPLE 6

A mixture of 3 ml of a 1 M sucrose solution, 3 ml of a 1 M glucose solution, 0.2 ml of a 0.5 M potassium phosphate buffer solution (pH 6.5), 2 ml of a 500 mM MES buffer solution (pH 6.5), 0.33 ml of the 10.8 unit/ml trehalose phosphorylase solution prepared in Preparation Example 1, 0.2 ml of a 17.8 unit/ml sucrose phosphorylase (Sigma, U.S.A.) solution, and 1.27 ml of purified water is incubated at 27.5° C. for 97 hours in a closed glass reactor. The resultant mixture is heated to inactivate the enzymes, subjected to the analytical procedure described in Example 2 and found to contain 283, 305, 18, and 10 mM of trehalose, fructose, glucose, and sucrose, respectively. The yield of trehalose from sucrose is calculated to be 94 mol %.

The HPLC elution pattern of the reaction products is shown in FIG. 1. The peaks corresponding to sucrose, glucose, trehalose, and fructose, which is a by-product, appear at 12.5, 9.9, 15.7, and 8.0 minutes, respectively.

EXAMPLE 7

A mixture of 300 μl of a 1 M sucrose solution, 300 μl of a 1 M glucose solution, 300 μl of a 500 mM MES buffer solution (pH 6.5), 150 μl of the 10.8 unit/ml trehalose phosphorylase solution prepared in Preparation Example 1, 150 μl of a 10.1 unit/ml sucrose phosphorylase (Sigma, U.S.A.) solution, and 300 μl of a solution, which consists of a phosphate buffer solution diluted with a calculated amount of purified water so that the eventual phosphate concentration becomes one of the values ranging from 0 to 100 mM, is incubated at 27.5° C. for 4 hours in an Eppendorf™ tube. The resultant mixture is heated to inactivate the enzymes, subjected to the analytical procedure described in Example 2 and found to give the results tabulated in Table 3. The results demonstrated that the optimal concentration of the inorganic phosphoric acid and/or salt thereof is 25 mM in these conditions.

TABLE 3

| | Phosphate Buffer | | Water | [Pi] | [Trehalose] |
|---|---|---|---|---|---|
| | conc.(mM) | vol.(μl) | (μl) | (mM) | (mM, theor.: 200) |
| 1 | 500 | 300 | 0 | 100 | 6.2 |
| 2 | 500 | 150 | 150 | 50 | 28.8 |
| 3 | 500 | 75 | 225 | 25 | 42.5 |
| 4 | 500 | 30 | 270 | 10 | 40.0 |
| 5 | 50 | 150 | 150 | 5 | 34.5 |
| 6 | 50 | 60 | 240 | 2 | 27.0 |
| 7 | 50 | 30 | 270 | 1 | 16.5 |
| 8 | 5 | 150 | 150 | 0.5 | 10.6 |
| 9 | 0 | 0 | 300 | 0 | 0 |

EXAMPLE 8

A mixture of 200 μl of a 600 mM glucose solution, 200 μl of a 60% dextrin (DE22) solution, 10 μl of a 125 mM potassium phosphate buffer solution (pH 6.5), 100 μl of a 500 mM MES buffer solution (pH 6.0), 40 μl of the potato α-phosphorylase solution prepared in Preparation Example 4, 40 μl of the 10.8 unit/ml trehalose phosphorylase solution prepared in Preparation Example 1, and 10 μl of purified water is incubated at 35° C. for 49 hours in an Eppendorf™ tube. The resultant mixture is treated with α-amylase and glucoamylase to convert maltose into glucose before being subjected to the analytical procedure described in Example 2. The reaction mixture is found to contain 73 mM of trehalose. The yield of trehalose is calculated to be 12.5 wt. % from dextrin and 70 wt. % from glucose.

EXAMPLE 9

In order to further purify trehalose prepared in Example 6, the enzymic reaction mixture is loaded on an activated charcoal column (25 mm ID×300 mm L, approximately 147 ml, chromatography grade, Wako Jun-yaku, K. K., Japan) to adsorb trehalose, washed with water, and eluted with 20% ethanol. Fractions containing trehalose are combined, concentrated under reduced pressure and subjected to an HPLC separation with a YMC-Pack™ Polyamine column (10 mm ID×250 mm L, YMC K. K., Japan) kept at 35° C., 5 ml/min. of an acetonitrile—water (70:30) solvent, and a differential refractometer kept at 35° C. The trehalose fractions, which have a retention time of 12.5 to 16.5 minutes, are combined and evaporated to dryness to give 750 mg of white powder.

The 250 MHz proton NMR spectral patterns of the white powder thus obtained are identical with those of commercially available trehalose. The white powder is found negative in the Somogyi-Nelson reducing sugar test. Furthermore, the white powder is dissolved in 0.05 N sulfuric acid to make a 20 mM solution, heated at 100° C. for 15 hours in a closed container to give 37 mM glucose according to an HPLC measurement.

What is claimed is:

1. A process for producing trehalose comprising:

mixing and reacting, in any order, (a) at least one α-phosphorylase capable of catalyzing production of α-glucose 1-phosphate from a saccharide raw material and at least one phosphorus source selected from the group consisting of an inorganic phosphoric acid and a salt thereof, (b) at least one trehalose phosphorylase, said trehalose phosphorylase having specific activity of about 0.086 units/mg-protein or greater and said trehalose phosphorylase being capable of catalyzing production of trehalose from α-glucose 1-phosphate and glucose, (c) at least one saccharide raw material which produces α-glucose 1-phosphate by catalytic action of the α-phosphorylase, (d) glucose, and (e) at least one phosphorus source selected from the group consisting of an inorganic phosphoric acid and a salt thereof; and harvesting said trehalose.

2. A process for producing trehalose comprising:

starting to incubate a saccharide raw material and at least one phosphorus source selected from the group consisting of an inorganic phosphoric acid and a salt thereof in the presence of an α-phosphorylase capable of catalyzing production of α-glucose 1-phosphate from said saccharide raw material and said phosphorus source to produce α-glucose 1-phosphate;

at any point of time after the formation of α-glucose 1-phosphate has started, and without separating α-glucose 1-phosphate, introducing glucose and at least one trehalose phosphorylase said trehalose phosphorylase having specific activity of about 0.086 units/mg-protein or greater and said trehalose phosphorylase being capable of catalyzing production of trehalose from α-glucose 1-phosphate and glucose to produce trehalose; and harvesting said trehalose.

3. A process for producing trehalose according to claim 1, wherein said at least one phosphorous source is mixed at a concentration of from 0.1 mmol to 6 mol per kg of the saccharide raw material.

4. A process for producing trehalose according to claim 1, wherein said α-phosphorylase is selected from the group consisting of starch phosphorylase, glycogen phosphorylase, 1,4-α-D-glucan phosphorylase, cellobiose phosphorylase, cellodextrin phosphorylase, 1,4-β-D-oligoglucan phosphorylase, laminaribiose phosphorylase, laminarin phosphorylase, 1,3-β-D-oligoglucan phosphorylase, 1,3-β-D-glucan phosphorylase, and sucrose phosphorylase.

5. A process for producing trehalose according to claim 1, wherein the saccharide raw material is capable of producing α-glucose 1-phosphate by catalytic action of the α-phosphorylase thereon in the presence of said at least one phosphorous source.

6. A process for producing trehalose according to claim 1, wherein the saccharide raw material capable of producing α-glucose 1-phosphate by the catalytic action of the α-phosphorylase thereon in the presence of said at least one phosphorous source is selected from the group consisting of starch, glycogen, dextrin, 1,4-α-D-glucan, cellobiose, cellodextrin, 1,4-β-D-oligoglucan, laminaribiose, laminarin, 1,3-β-D-glucan, and sucrose.

7. A process for producing trehalose according to claim 1, wherein the trehalose phosphorylase is originated in a material selected from the group consisting of Schizophyllum, Pleurotus, Grifola, Agaricus, Trametes, Coriolus, Trichaptumand Lenzites.

8. A process for producing trehalose according to claim 1, wherein the trehalose phosphorylase is originated in a material selected from the group consisting of *Schizophyllum commune, Pleurotus ostreatus, Grifola frondosa, Agaricus bisporus, Trametes versicolor, Coriolus versicolor, Trametes hirsuta, Coriolus hirsutus, Coriolus consors, Trichaptum biforme,* and *Lenzites betulina.*

9. A process according to claim 1, wherein said saccharide raw material is mixed at a concentration of 0.1 to 75 kg per 100 l reaction mixture.

10. A process according to claim 1, wherein said glucose is mixed at a concentration of 0.01 to 50 kg per 100 l reaction mixture.

11. A process according to claim 1, wherein said at least one α-phosphorylase is mixed at a concentration of at least 0.1 units per kg of saccharide raw material.

12. A process according to claim 1, wherein said at least one trehalose phosphorylase is mixed at a concentration of at least 0.1 units per kg of saccharide raw material.

13. A process according to claim 1, wherein said saccharide raw material is mixed at a concentration of 0.1 to 75 kg per 100 l reaction mixture, said glucose is mixed at a concentration of 0.01 to 50 kg per 100l reaction mixture, and said phosphorous source is mixed at a concentration of 0.0001 to 6 mol per kg of said saccharide raw material.

14. A process for producing trehalose according to claim 1, wherein α-glucose 1-phosphate is produced by the catalytic action of an α-phosphorylase selected from the group consisting of potato phosphorylase and sucrose phosphorylase on the saccharide raw material in the presence of said at least one phosphorous source followed by reaction with glucose in the presence of a trehalose phosphorylase from *Grifola frondosa.*

15. A process according to claim 3, wherein said concentration of said phosphorous source is 1 mmol to 0.5 mol per kg of saccharide raw material.

16. A process according to claim 7, wherein said concentration of said saccharide raw material is 0.5 to 50 kg per 100 l reaction mixture.

17. A process according to claim 8, wherein said concentration of said glucose is 1 to 25 kg per 100 l reaction mixture.

18. A process according to claim 12, wherein said at least one α-phosphorylase and said at least one trehalose phosphorylase each are mixed at a concentration of at least 0.1 units per kg of saccharide raw material.

19. A process for producing trehalose comprising incubating saccharide raw material and at least one phosphorus source selected from the group consisting of an inorganic phosphoric acid and a salt thereof, in the presence α-phosphorylase to produce α-glucose 1-phosphate;

separating the α-glucose 1-phosphate produced; then reacting the α-glucose 1-phosphate with glucose in the presence of at least one trehalose phosphorylase, said trehalose phosphorylase having specific activity of about 0.086 units/mg-protein or greater and said trehalose phosphorylase being capable of catalyzing production of trehalose from α-glucose 1-phosphate and glucose; and harvesting said trehalose.

20. A process for producing trehalose comprising mixing and reacting, in any order, (a) at least one α-phosphorylase capable of catalyzing production of α-glucose 1-phosphate from a saccharide raw material and at least one phosphorus source selected from the group consisting of an inorganic phosphoric acid and a salt thereof, (b) at least one trehalose phosphorylase, said trehalose phosphorylase being derived from a trehalose phosphorylase gene originating in Lyophyllum and said trehalose phosphorylase being capable of catalyzing production of trehalose from α-glucose 1-phosphate and glucose; and harvesting said trehalose.

21. A process for producing trehalose according to claim 1, wherein the trehalose phosphorylase is derived from a gene originating in the class Basidiomycetes.

\* \* \* \* \*